(12) United States Patent
Fujimoto et al.

(10) Patent No.: US 7,972,792 B2
(45) Date of Patent: Jul. 5, 2011

(54) SEQUENCE-SPECIFIC NUCLEIC ACID PURIFICATION METHOD MANNER

(75) Inventors: Kenzo Fujimoto, Nomi (JP); Yoshinaga Yoshimura, Nomi (JP)

(73) Assignees: Japan Advanced Institute of Science and Technology, Momi-shi (JP); Japan Science and Technology Agency, Kawaguchi-shi (JP)

( * ) Notice: Subject to any disclaimer, the term of this patent is extended or adjusted under 35 U.S.C. 154(b) by 0 days.

(21) Appl. No.: 12/937,471

(22) PCT Filed: Apr. 16, 2009

(86) PCT No.: PCT/JP2009/001747
§ 371 (c)(1),
(2), (4) Date: Oct. 12, 2010

(87) PCT Pub. No.: WO2009/128266
PCT Pub. Date: Oct. 22, 2009

(65) Prior Publication Data
US 2011/0034683 A1    Feb. 10, 2011

(30) Foreign Application Priority Data
Apr. 16, 2008   (JP) ................................. 2008-106642

(51) Int. Cl.
*C12Q 1/68* (2006.01)
*C07H 21/02* (2006.01)
*C07H 21/04* (2006.01)

(52) U.S. Cl. .......... 435/6; 536/23.1; 536/24.3; 536/26.6

(58) Field of Classification Search ..... 435/6; 536/24.3, 536/26.6, 23.1
See application file for complete search history.

(56) References Cited

U.S. PATENT DOCUMENTS
6,593,088 B1    7/2003   Saito et al.

FOREIGN PATENT DOCUMENTS
JP    2001-139594 A    5/2001
JP    2001-348398 A    12/2001

OTHER PUBLICATIONS

Notification of Transmittal of Translation of the International Preliminary Report on Patentability (Form PCT/ IB/338 of International Application No. PCT/JP2009/001747 mailed Dec. 9, 2010 with Forms PCT/IB/373 and PCT/ISA/237.

(Continued)

*Primary Examiner* — Jezia Riley
(74) *Attorney, Agent, or Firm* — Westerman, Hattori, Daniels & Adrian, LLP

(57) ABSTRACT

Disclosed is a method for the purification and collection of a nucleic acid comprising a specific nucleotide sequence, which can be carried out within an extremely short period and can achieve both high sequence-specificity and a high collection rate. Specifically disclosed is a method for the purification of a target nucleic acid comprising a specific nucleotide sequence and contained in a nucleic acid mixture. The method comprises the steps of: hybridizing a photo-ligating nucleic acid having a group represented by formula (I) as abase moiety with the target nucleic acid to form a hybrid; irradiating the hybrid of the photo-ligating nucleic acid and the target nucleic acid with light to cause the photo-ligation of the hybrid; removing any un-photo-ligated nucleic acid by washing; and irradiating the hybrid of the photo-ligating nucleic acid and the target nucleic acid with light to cause the photo-cleavage of the hybrid.

9 Claims, 9 Drawing Sheets

Structure of 3-cyanovinylcarbazole-1'-β-deoxyriboside.

OTHER PUBLICATIONS

Yoshimura, Y. et al. "Cyanovinyl Carbazole Gan'yu Kakusan o Mochiite Hikari Kagyakuteki DNA Cross Link Hanno," The Society of Polymer Science, Japan Hokuriku Shibu Kenkyu Happyo Koenkai Koen Yoshishu, Nov. 15, 2008, vol. 57, p. 133, cited in ISR.

Yoshimura, Y. et al. "Catalyic Repair of a Thymine Dimer in DNA via Carbazole Nucleoside," Chemistry Letters, Feb. 1, 2006, vol. 35, No. 4, pp. 386-387, cited in ISR.

Kyoi, Y. et al "Hikari Otosei Cytosine Yudotai o Mochiita DNA Ichi Enki Tagata no Kenshutsu," 87th Annual Meeting on Chemical Society of Japan in Spring 2007, Koen Yokoshu II, Mar. 12, 2007, Yoko Bango 2 J2-50, p. 1292, cited in ISR.

Takehiro A. et al. "Hikari Renketsusei o Motsu Keiko Enki o Fukumu Kakusan Gosei," 85th Annual Meeting on Chemical Society of Japan in Spring 2005, Koen Yokoshu II, Mar. 11, 2005, Yoko Bango 1 PB-107, p. 1474, cited in ISR.

Yoshimura, Y. et al. "Carbazole Gan'yu Kakusan o Mochiita Thymine Dimer no Shokubaiteki Hikari Shufuku Hanno ," Polymer Preprints Japan, Sep. 5, 2006, vol. 55 No. 2, p. 4840, cited in ISR.

Yoshimura, Y. et al. "Ultrafast Reversible Photo-Cross-Linking Reaction: Toward in Situ DNA Manipulation," Organic Letters, May 14, 2008, vol. 10 No. 15, pp. 3227-3230, cited in ISR.

Yoshimura, Y. et al "Hikari Zokanzai Gan'yu Kakusan o Riyo shita Hikari Kagyakuteki Idenshi Sosaho no Kaihatsu," The Society of Polymer Science, Japan Hokuriku Shibu Kenkyu Happyo Koenkai Koen Yoshishu, Nov. 15, 2008, vol. 57, p. 136, cited in ISR.

Fujimoto, K. et al "A Light-Controlled Reversible DNA Photoligation via Carbazole-Tethered 5-Carboxyvinyluracil," Organic Letters, Nov. 5, 2007, vol. 10, No. 3, pp. 397-400, cited in ISR.

International Search Report of PCT/JP2009/001747, mailing date Jun. 2, 2009.

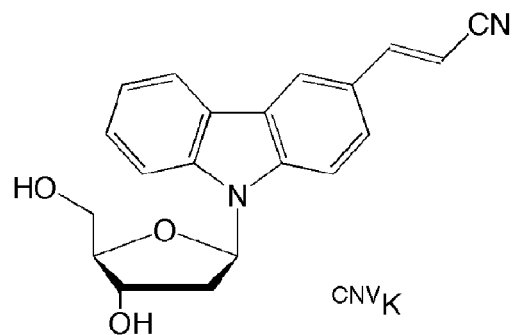
Figure 1. Structure of 3-cyanovinylcarbazole-1'-β-deoxyriboside.
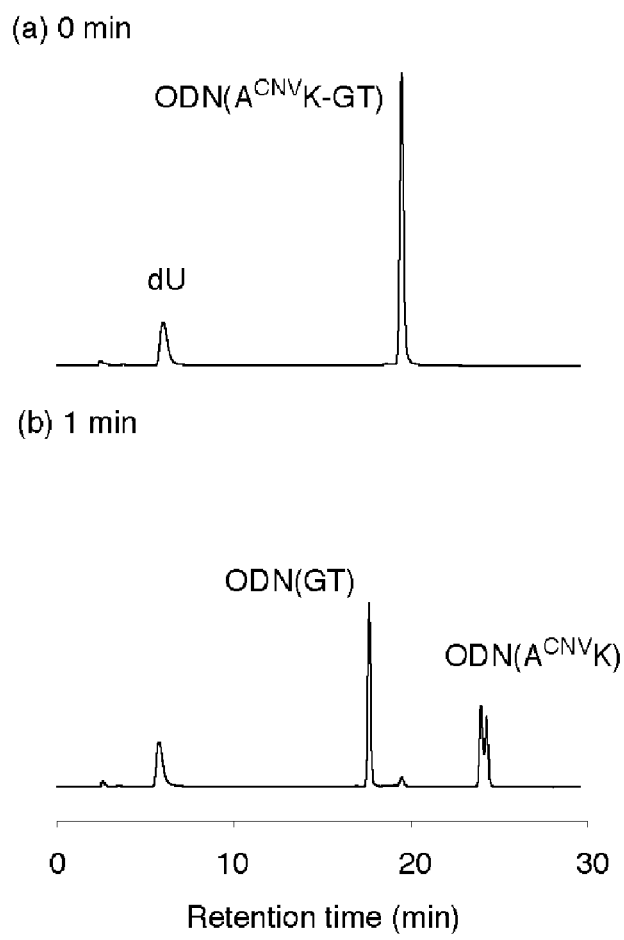
Figure 2. HPLC analysis.

(a) 0 min

ODN(G$^{CNV}$K-GC)

dU (b) 3 min

ODN(GC)

ODN(G$^{CNV}$K)

Retention time (min)

Figure 3. HPLC analysis.

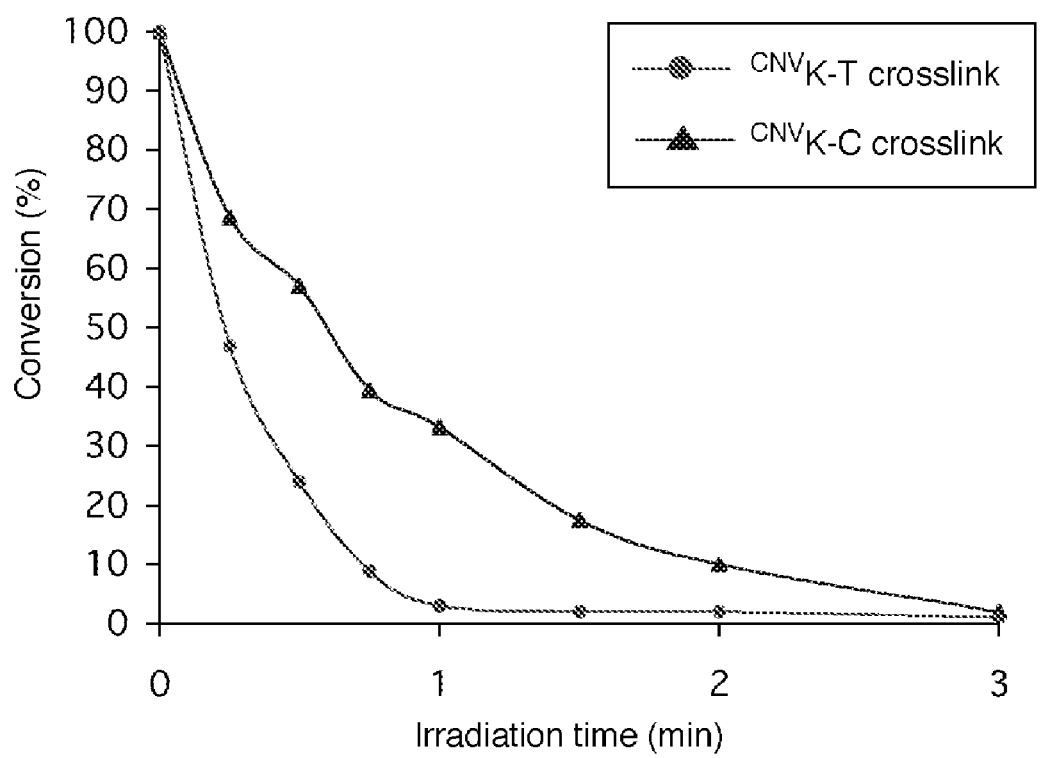
Figure 4. Time course of photosplitting of ODN(A$^{CNV}$K-GT) (●) and ODN(G$^{CNV}$K-GC) (▲).

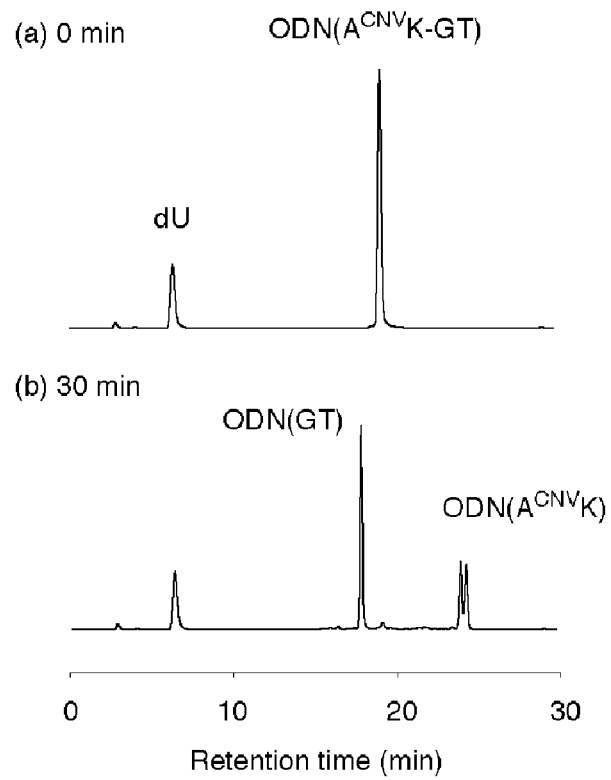
Figure 5. HPLC analysis
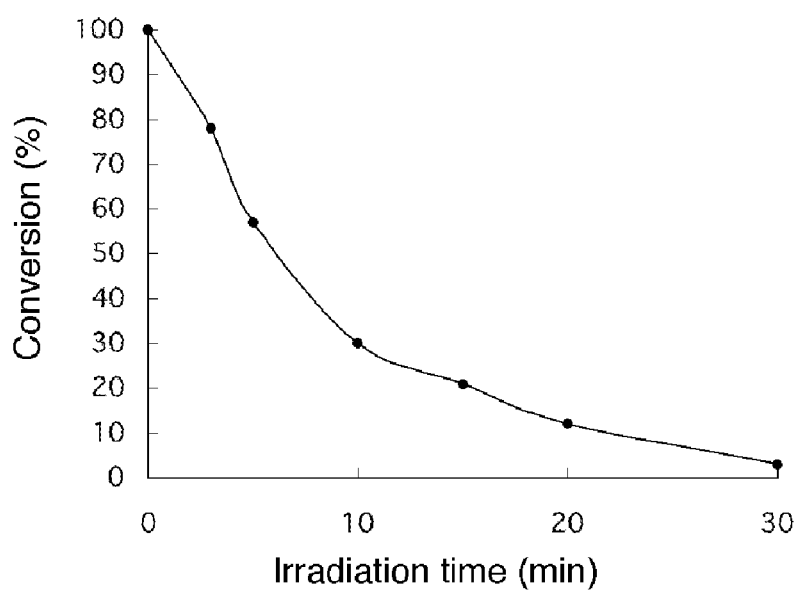
Figure 6. Time course of photosplitting of ODN($A^{CNV}$K-GT).

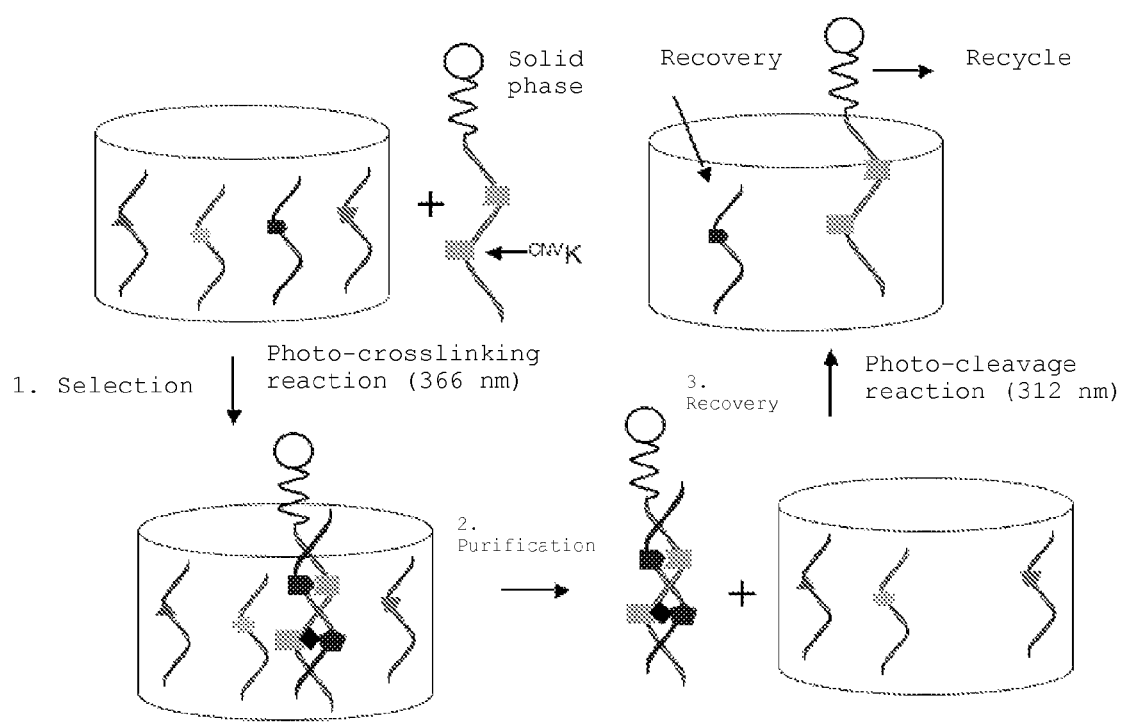
Figure 7. Strategy for the sequence specific purification of DNA.

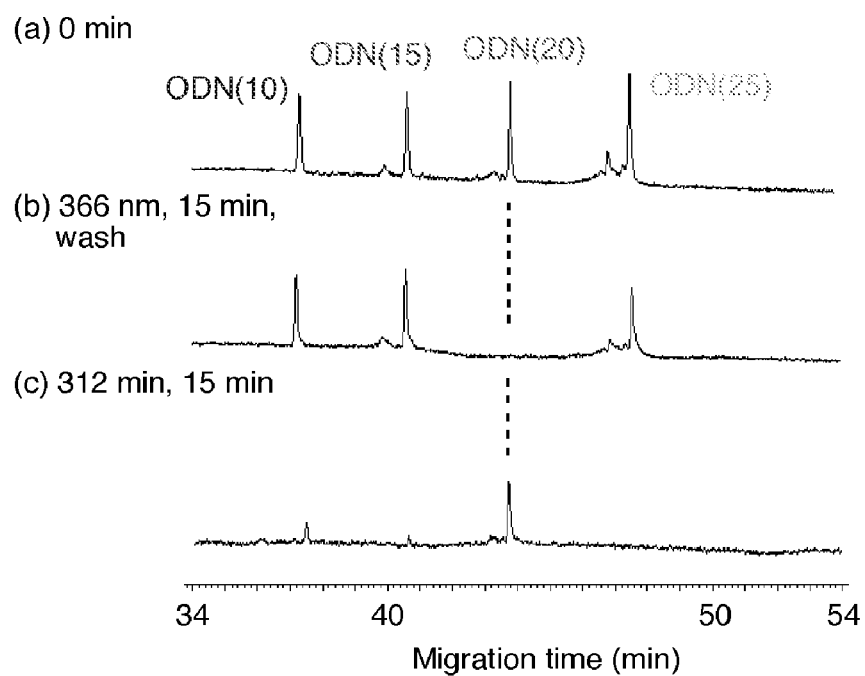
Figure 8. CGE analysis.
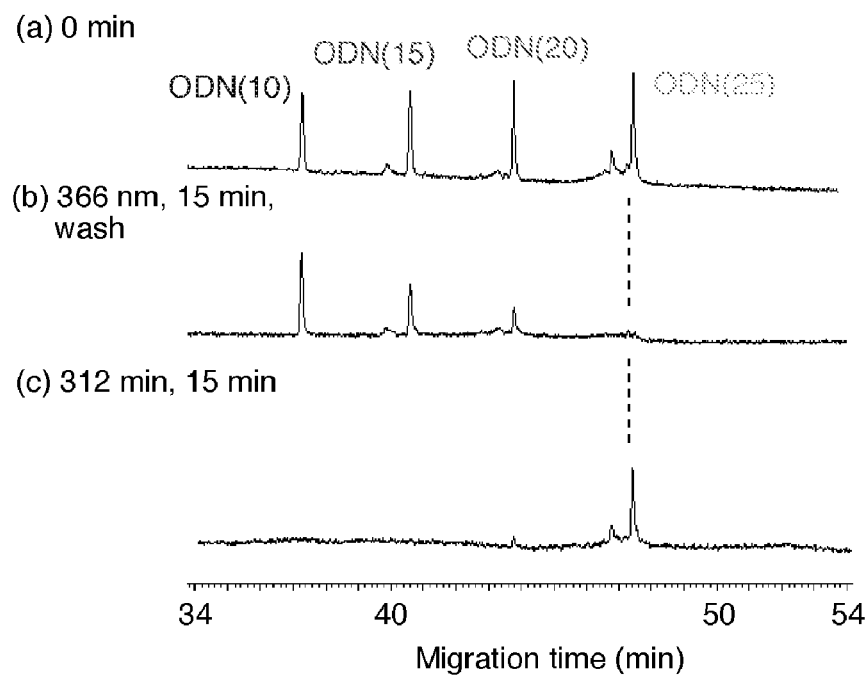
Figure 9. CGE analysis.

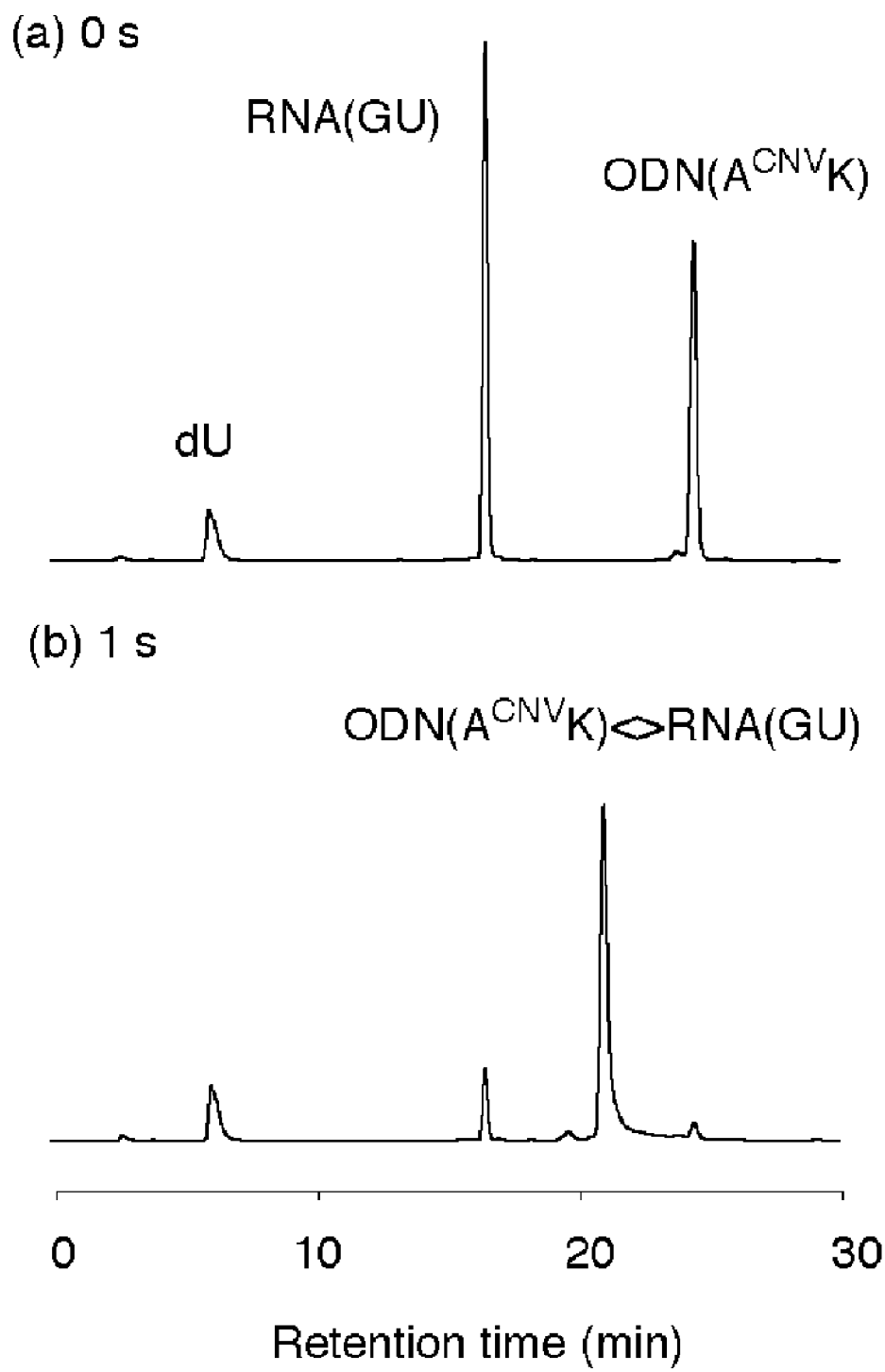
Figure 10. HPLC analysis.

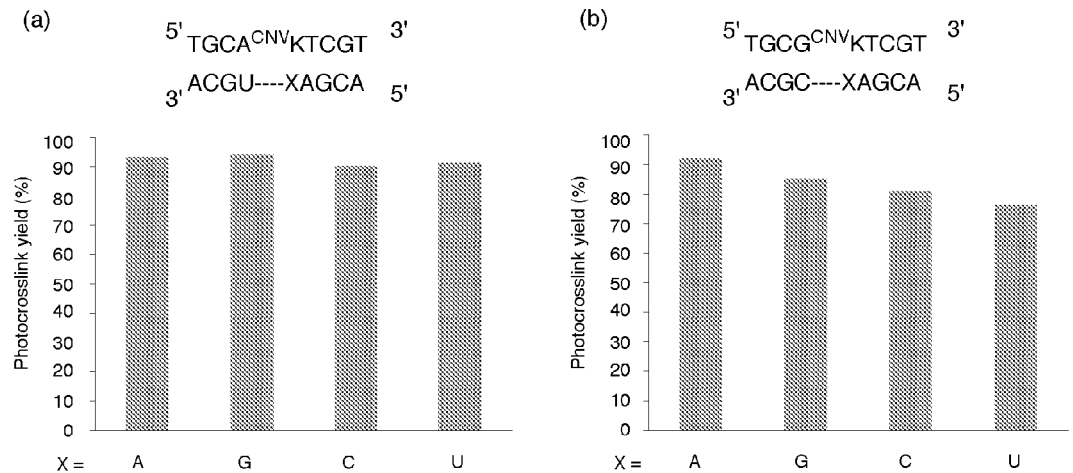
Figure 11. Photocrosslinking reaction of various sequences.
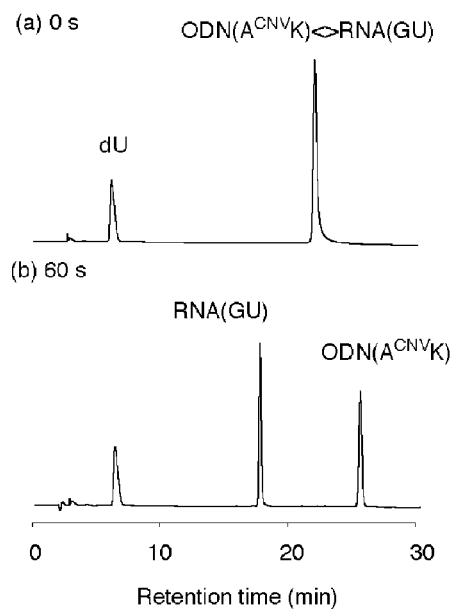
Figure 12. HPLC analysis.

(a) 0 s
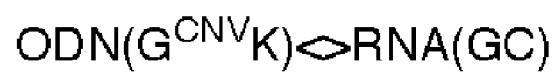
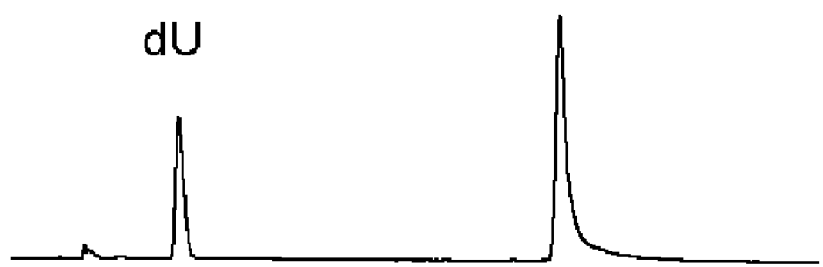
(b) 3 min
Figure 13. HPLC analysis.

SEQUENCE LISTING

```
<160> NUMBER OF SEQ ID NOS: 7

<210> SEQ ID NO 1
<211> LENGTH: 10
<212> TYPE: DNA
<213> ORGANISM: Artificial
<220> FEATURE:
<223> OTHER INFORMATION: ODN(10) in Scheme 4

<400> SEQUENCE: 1
cgcgttttca                                                      10

<210> SEQ ID NO 2
<211> LENGTH: 15
<212> TYPE: DNA
<213> ORGANISM: Artificial
```

```
-continued

<220> FEATURE:
<223> OTHER INFORMATION: ODN(15)

<400> SEQUENCE: 2
tagccctttc tccta                                                    15

<210> SEQ ID NO 3
<211> LENGTH: 20
<212> TYPE: DNA
<213> ORGANISM: Artificial
<220> FEATURE:
<223> OTHER INFORMATION: ODN(20)

<400> SEQUENCE: 3
cacgcttcat cccatttcga                                               20

<210> SEQ ID NO 4
<211> LENGTH: 25
<212> TYPE: DNA
<213> ORGANISM: Artificial
<220> FEATURE:
<223> OTHER INFORMATION: ODN(25)

<400> SEQUENCE: 4
gcggaagtta ctcgataaag ggtat                                         25

<210> SEQ ID NO 5
<211> LENGTH: 10
<212> TYPE: DNA
<213> ORGANISM: Artificial
<220> FEATURE:
<223> OTHER INFORMATION: ODN(10) in Scheme 5

<400> SEQUENCE: 5
cgcgtttcct                                                          10

<210> SEQ ID NO 6
<211> LENGTH: 9
<212> TYPE: DNA
<213> ORGANISM: Artificial
<220> FEATURE:
<223> OTHER INFORMATION: ODN1(CNVK)-PS
<220> FEATURE:
<221> NAME/KEY: modified_base
<222> LOCATION: (5)..(5)
<223> OTHER INFORMATION: n stands for 3-cyanovinylcarbazole-1'-beta-
      deoxyriboside
<220> FEATURE:
<221> NAME/KEY: misc_feature
<222> LOCATION: (9)..(9)
<223> OTHER INFORMATION: n stands for t linked to polystylene beads(PS)
      via linker(SSS)

<400> SEQUENCE: 6 atgangcgn                                                            9

<210> SEQ ID NO 7
<211> LENGTH: 9
<212> TYPE: DNA
<213> ORGANISM: Artificial
<220> FEATURE:
<223> OTHER INFORMATION: ODN2(CNVK)-PS
<220> FEATURE:
<221> NAME/KEY: modified_base
<222> LOCATION: (5)..(5)
<223> OTHER INFORMATION: n stands for 3-cyanovinylcarbazole-1'-beta-
      deoxyriboside
<220> FEATURE:
<221> NAME/KEY: misc_feature
<222> LOCATION: (9)..(9)
```

```
<223> OTHER INFORMATION: n stands for c linked to polystylene beads(PS)
      via linker(SSS)

<400> SEQUENCE: 7 gtaanttcn                                                              9
```

SEQUENCE-SPECIFIC NUCLEIC ACID PURIFICATION METHOD MANNER

TECHNICAL FIELD

The present invention relates to a method for the sequence-specific purification of nucleic acids.

BACKGROUND ART

Purification and recovery of a nucleic acid having a particular base sequence is one of the basic techniques that are important in the field of genetic engineering. In the purification and recovery of a nucleic acid having a particular base sequence, the formation of a hybrid (hybridization) with a nucleic acid probe having a base sequence that is complementary to the particular sequence, has been long used as a fundamental principle which allows specific recognition of a particular base sequence (see, for example, Non-Patent Document 1).

However, under the actual conditions for the hybrid formation, it is difficult to induce the association with the nucleic acid probe molecule only by means of the nucleic acid of the target base sequence that hybridizes as a complete complementary chain. That is, it is known that even a nucleic acid having a non-target base sequence that is incomplete as a complementary chain, undergoes incomplete hybridization including certain mismatches, and association with the nucleic acid probe molecule occurs. Such an unintended association with the nucleic acid probe (error) will appear as a noise (impurity) in the subsequent recovery stage. In order to increase the specificity of detection so as to prevent the appearance of this noise, it is necessary to eliminate incomplete hybridization.

On the other hand, in order to reduce the noise (impurity), the treatment may be carried out under the conditions which do not allow incomplete hybridization as far as possible; however, under such conditions, the intended hybridization is also unstabilized. As a result, the recovery rate of a target nucleic acid is decreased.

However, the discrimination by hybridization makes use of the difference in the thermal stability in an equilibrium system, and the difference between the complete hybridization and the incomplete hybridization is merely a difference in the thermal stability. Therefore, the conditions appropriate for discriminating the two vary with the target base sequence, and even under appropriate conditions, the conditions that alter the thermal stability act equally on both. Even under the experimental conditions in which strict temperature management has been conducted, this fact does not change. That is, as long as only the difference in the thermal stability of hybridization in an equilibrium system is used as the principle of discrimination of the two, even if an experiment is performed under the experimental conditions with the conditions of temperature management or the like strictly set, a certain noise (impurities) had to be put up with by making compromise in the balance between the degree of purification and the recovery rate.

Moreover, in recent years, there is a demand for a technology intended to achieve the purification and recovery of a nucleic acid having a single-base-substituted base sequence, for the purpose of new drug development or genetic diagnosis. Particularly, a technology for typing single nucleotide polymorphism of DNA is under high expectation in the field of medical diagnosis. Therefore, there is a special demand for a technology for purification and recovery, which achieves a good balance between high sequence specificity to the extent capable of discriminating single base substitution, and a practically useful recovery rate.

In recent years, there is also a demand for a technology intended to achieve the purification and recovery of an RNA that is not translated, which is generally referred to as non-coding RNA (ncRNA). This ncRNA includes one group called microRNA (miRNA) because of the small size of the molecules, and furthermore, a significant portion of the molecules which have been traditionally regarded as mRNA simply because the molecules have polyA and is frequently subjected to splicing, is said to belong to a group called mRNA-like ncRNA. However, since these RNAs exist in many species, with small numbers of molecules, and also since the RNAs are susceptible to degradation and short-lived, purification and recovery thereof must be carried out in a very short time. For this reason, a technology for sequence-specific purification and recovery of RNA, which can be carried out in a very short time, is especially in demand.

Non-Patent Literature 1: Lambert, K. N., Williamson, V. M. Nucleic Acids Res., 1993, 21, pp. 775-776.

SUMMARY OF THE INVENTION

Problems to be Solved by the Invention

Therefore, it is an object of the present invention to provide a method for the purification and recovery of a nucleic acid having a particular base sequence, which can be carried out in a very short time and achieves a good balance between high sequence-specificity and high recovery rate.

Means for Solving the Problems

For the object described above, the inventors of the present invention conceived an idea of using the photo-ligating technology, which has long been a subject of thorough research and development. The inventors then found that the novel artificial base (artificial nucleobase) developed by the present inventors is capable of photo-ligation and photo-cleavage, and these processes can be achieved through light irradiation for a very short time. Thus, the inventors found that when hybridization, photo-ligation and photo-cleavage of a nucleic acid are carried out in combination using this artificial base (artificial nucleobase), the object described above can be achieved.

That is, a sample nucleic acid and a probe which are covalently linked through photo-ligation using a novel artificial base by specifically performing photo-ligation only when complete hybridization has been achieved, now without depending on the maintenance of the hybridization, are sufficiently washed under the conditions which lead to the dissociation of a complementary double-strand, and then the covalently linked sample nucleic acid and the probe was subjected to photo-cleavage. Thus, a good balance between high sequence-specificity and high recovery rate was achieved, and thereby the purification and recovery of a nucleic acid having a particular base sequence could be carried out. This purification and recovery can be carried out in a very short time by photo-ligating and photo-cleaving the novel artificial base.

Thus, the present invention includes the following items [1] to [9].

[1] A method of purifying a target nucleic acid having a particular base sequence that is contained in a nucleic acid mixture, the method comprising:

hybridizing a photo-ligating nucleic acid (wherein the nucleic acid includes a nucleic acid and a peptide nucleic acid) having a group represented by the following formula (I) as a base moiety:

[Chemical Formula 1]

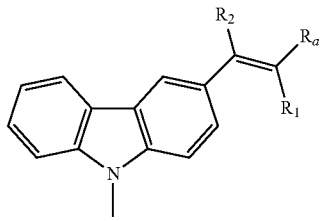

(I)

(wherein in the formula (I), Ra represents a cyano group, an amide group, a carboxyl group, a C2-C7 alkoxycarbonyl group or hydrogen; and
R1 and R2 each independently represent a cyano group, an amide group, a carboxyl group, a C2-C7 alkoxycarbonyl group or hydrogen),
with the target nucleic acid having a particular base sequence that is contained in a nucleic acid mixture;
irradiating the hybrid of the photo-ligating nucleic acid and target nucleic acid with light to induce photo-ligation of the hybrid;
removing any un-photo-ligated nucleic acid by washing; and
irradiating the hybrid of the photo-ligating nucleic acid and the target nucleic acid with light to induce photo-cleavage of the hybrid.

[2] The method according to the item [1], wherein the step of removing any un-photo-ligated nucleic acid by washing is carried out by washing under the washing conditions in which a complementary double strand is dissociated.

[3] The method according to any one of the items [1] and [2], wherein the photo-ligating nucleic acid has a labeling site.

[4] The method according to any one of the items [1] and [2], wherein the photo-ligating nucleic acid is immobilized onto a support.

[5] The method according to any one of the items [1] to [4], wherein the light irradiation of the step of inducing photo-ligation is carried out by irradiation with light having a wavelength in the range of 350 to 380 nm.

[6] The method according to any one of the items [1] to [5], wherein the light irradiation of the step of inducing photo-cleavage is carried out by irradiation with light having a wavelength in the range of 310 to 345 nm.

[7] The method according to any one of the items [1] to [6], wherein the step of inducing photo-ligation is carried out in a reaction solution containing a salt having a buffering action.

[8] A photo-ligating nucleic acid (wherein the nucleic acid includes a nucleic acid and a peptide nucleic acid) having a labeling site and having a group represented by the following formula (I) as a base moiety:

[Chemical Formula 2]

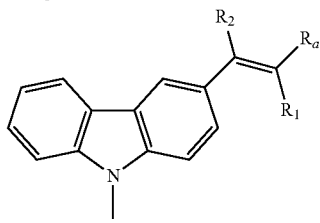

(I)

wherein in the formula (I), Ra represents a cyano group, an amide group, a carboxyl group, a C2-C7 alkoxycarbonyl group, or hydrogen; and R1 and R2 each independently represent a cyano group, an amide group, a carboxyl group, a C2-C7 alkoxycarbonyl group, or hydrogen.

[9] A photo-ligating nucleic acid (wherein the nucleic acid includes a nucleic acid and a peptide nucleic acid) immobilized onto a support and having a group represented by the following formula (I) as a base moiety:

[Chemical Formula 3]

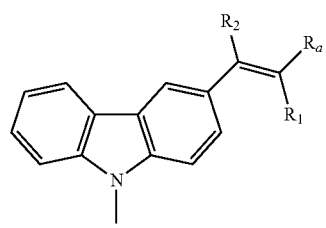

(I)

wherein in the formula (I), Ra represents a cyano group, an amide group, a carboxyl group, a C2-C7 alkoxycarbonyl group, or hydrogen; and
R1 and R2 each independently represent a cyano group, an amide group, a carboxyl group, a C2-C7 alkoxycarbonyl group, or hydrogen.

Effects of the Invention

According to the present invention, purification and recovery of a nucleic acid having a particular base sequence can be carried out while achieving a good balance between high sequence-specificity and high recovery rate. Therefore, the purification and recovery of a nucleic acid having a single-base-substituted base sequence, which is attracting attention for the purpose of new drug development or genetic diagnosis, can also be achieved.

Furthermore, the purification and recovery according to the present invention can be carried out in a very short time, by photo-ligating (photo-linking) and then photo-cleaving an artificial base. Therefore, even an RNA which is susceptible to degradation and is short-lived, can also be subjected to purification and recovery.

As such, since the purification and recovery according to the present invention can achieve a good balance between high sequence-specificity and high recovery rate and can be carried out in a short time, a way to the isolation and purification has been pioneered even for a non-coding RNA (ncRNA), which particularly exists in many species, with small numbers of molecules, and which is susceptible to degradation and is short-lived. Particularly, the purification and recovery according to the present invention can be widely applied even to an RNA that does not have the so-called polyA, and therefore, the present invention is innovative.

BRIEF DESCRIPTION OF THE DRAWINGS

FIG. 1 is a diagram showing the structural formula of 3-cyanovinylcarbazole-1'-β-deoxyriboside ($^{CNV}$K), which is a photoresponsive nucleic acid;

FIG. 2(*a*) and FIG. 2(*b*) are diagrams showing the results of an analysis by HPLC of a photo-cleavage product of ODN ($A^{CNV}$K-GT);

FIG. 3(*a*) and FIG. 3(*b*) are diagrams showing the results of an analysis by HPLC of a photo-cleavage product of ODN ($G^{CNV}$K-GC);

FIG. 4 is a diagram showing the changes over time in the photo-cleavage of a photo-cross linked product;

FIG. 5(a) and FIG. 5(b) are diagrams showing the results of an analysis by HPLC of a photo-cleavage product of ODN ($A^{CNV}K$-GT);

FIG. 6 is a diagram showing the changes over time in the photo-cleavage of a photo-cross linked product;

FIG. 7 is an explanatory diagram schematically showing an example of the sequence-specific purification of a DNA;

FIG. 8(a), FIG. 8(b) and FIG. 8(c) are diagrams showing the results of sequence-specific purification of a DNA;

FIG. 9(a), FIG. 9(b) and FIG. 9(c) are diagrams showing the results of sequence-specific purification of a DNA;

FIG. 10(a) and FIG. 10(b) are diagrams showing the results of an analysis by HPLC of a product obtained by a photo-crosslinking reaction;

FIG. 11(a) and FIG. 11(b) are diagrams showing the results of an experiment to identify the bases of RNAs that are capable of photo-crosslinking;

FIG. 12(a) and FIG. 12(b) are diagrams showing the results of an analysis by HPLC of a photo-cleavage product of ODN ($A^{CNV}K$)<>RNA (GU); and FIG. 13(a) and FIG. 13(b) are diagrams showing the results of an analysis by HPLC of a photo-cleavage product of ODN ($G^{CNV}K$)<>RNA (GC).

MODES FOR CARRYING OUT THE INVENTION

The present invention will be described below in detail byway of an embodiment of the present invention. The present invention is not intended to be limited to the embodiment illustrated below.

The present invention lies in a method for purifying a target nucleic acid having a particular base sequence that is contained in a nucleic acid mixture, the method including the steps of:

hybridizing a photo-ligating nucleic acid (wherein the nucleic acid includes a nucleic acid and a peptide nucleic acid) having a group represented by the following formula (I) as a base moiety:

[Chemical Formula 4]

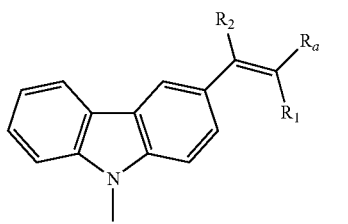

(I)

(wherein in the formula (I), Ra represents a cyano group, an amide group, a carboxyl group, a C2-C7 alkoxycarbonyl group or hydrogen; and R1 and R2 each independently represent a cyano group, an amide group, a carboxyl group, a C2-C7 alkoxycarbonyl group or hydrogen), with the target nucleic acid having a particular base sequence that is contained in a nucleic acid mixture;

irradiating the hybrid of the photo-ligating nucleic acid and target nucleic acid with light to induce photo-ligation of the hybrid;

removing any un-photo-ligated nucleic acid by washing; and irradiating the hybrid of the photo-ligating nucleic acid and the target nucleic acid with light to induce photo-cleavage of the hybrid.

Through such processes, the purification and recovery according to the present invention can achieve a good balance between high sequence specificity and a high recovery rate, and can be carried out in a short time.

Ra in the formula (I) represents a cyano group, an amide group, a carboxyl group, an alkoxycarbonyl group or hydrogen. Ra is preferably a cyano group, an amide group, a carboxyl group, an alkoxycarbonyl group or hydrogen, and more preferably a cyano group, an amide group, a carboxyl group or an alkoxycarbonyl group. Regarding the alkoxycarbonyl group, an alkoxycarbonyl group preferably having 2 to 7 carbon atoms, more preferably 2 to 6 carbon atoms, even more preferably 2 to 5 carbon atoms, even more preferably 2 to 4 carbon atoms, still more preferably 2 to 3 carbon atoms, and particularly preferably 2 carbon atoms, can be used.

R1 and R2 in the formula (I) each independently represent a cyano group, an amide group, a carboxyl group, an alkoxycarbonyl group, or hydrogen. R1 and R2 are preferably each a cyano group, an amide group, a carboxyl group, an alkoxycarbonyl group, or hydrogen, and more preferably a cyano group, an amide group, a carboxyl group, or an alkoxycarbonyl group. Regarding the alkoxycarbonyl group, an alkoxycarbonyl group preferably having 2 to 7 carbon atoms, more preferably 2 to 6 carbon atoms, even more preferably 2 to 5 carbon atoms, even more preferably 2 to 4 carbon atoms, still more preferably 2 to 3 carbon atoms, and particularly preferably 2 carbon atoms, can be used.

The group represented by the formula (I) shown above is a novel artificial base (artificial nucleobase) according to the present invention. A nucleic acid having this group as a base moiety acquires photo-ligating properties through this group. Since such photo-ligating properties are imparted when a molecule carries the artificial nucleobase as a base moiety, such photo-ligating properties can be imparted to a nucleic acid (DNA, RNA) or even to a peptide nucleic acid. The photo-ligating nucleic acid can be produced according to a conventional method for the production of nucleic acid.

A nucleic acid that has been imparted with photo-ligating properties (photo-ligating nucleic acid) can be hybridized with a nucleic acid having a sequence complementary to the sequence of the foregoing nucleic acid, in the same manner as in the case of conventional nucleic acids. That is, the photo-ligating nucleic acid can be hybridized with a nucleic acid having a particular base sequence (target nucleic acid) among a mixture of a number of nucleic acids. In other words, the photo-ligating nucleic acid is produced to serve as a nucleic acid having a base sequence that is complementary to the base sequence of the target nucleic acid having a particular base sequence.

When the photo-ligating nucleic acid is hybridized with the target nucleic acid, the type of the base placed at the position which forms a base pair with the artificial base represented by the formula (I) is not limited. Even though any of A, T, C, G and U is placed at the position of the counterpart base that interacts with the artificial base (K) represented by the formula (I), the photo-ligating nucleic acid and the target nucleic acid can satisfactorily form a hybrid. The artificial base represented by the formula (I) may be placed at any position in the base sequence of a nucleic acid. The photo-ligating nucleic acid and the target nucleic acid may be nucleic acids of the same type, or may be nucleic acids of different types, as long as they can form a hybrid.

The base in a counterpart nucleic acid with which a photo-ligating nucleic acid can be photo-ligated via the artificial base represented by the formula (I), is a base having a pyrimidine ring. That is, the base may be T, C or U. As such, since U is also subjected to photo-ligation, it should be noted that the present invention can be suitably carried out using RNA as a target nucleic acid. As it is demonstrated in the Examples, the photo-ligation according to the present invention occurs on the base that is placed at the position in the chain of the counterpart, only one base away toward the 3'-terminus from the position of the counterpart base that interacts with the artificial base (K) represented by the formula (I).

In a preferable embodiment, the photo-ligating nucleic acid may have a labeling site (a labeling moiety). For the labeling site, various labels can be used, and examples that can be used include a biotin label, a dye label (including a fluorescent dye label), an RI label, and an enzyme label (including a color developing enzyme label). When the photo-ligating nucleic acid has such a label site, the photo-ligating nucleic acid in the state of being crosslinked with the target nucleic acid can be easily isolated and recovered.

Preferred as the label used for such a labeling moiety is a label that can endure sufficient washing that may possibly occur in the present invention. From the viewpoint of the ease of handling and the resistance to the severe washing conditions, a biotin label or a fluorescent dye label is preferred. The biotin label can be further recovered by detecting through the biotin-avidin bond, or by immobilizing, using various labels having an avidin moiety. The addition of these label moieties can be carried out according to conventional production methods. It is usually preferable for the photo-ligating nucleic acid to have a label moiety near the terminals, but the photo-ligating nucleic acid may also have a label moiety at any other site as long as the label moiety does not have adverse effects on photo-ligation and hybridization.

In a preferable embodiment, the photo-ligating nucleic acid may be immobilized onto a support (a carrier or a base material). When a photo-ligating nucleic acid immobilized onto a support as such is used, the photo-ligated target nucleic acid is immobilized onto the support and can be easily isolated and recovered. As the support, materials of various qualities such as those used as solid phase supports in the field of biochemistry, can be used. Examples include inorganic materials such as glass and porous glass; resins such as polystyrene (PS); and metals such as gold. Preferred materials include a solid phase support having an adenosine residue (oligo-affinity support (OAS) or the like), aldehyde-modified glass, and the like. A glass plate, CPG, polystyrene beads and the like are preferable. Conventional materials that are used as the substrate of DNA chips can be suitably used. These materials can be fabricated into various shapes that are conventionally used for such purposes, and can be fabricated into, for example, a bead shape, a particulate shape, a cylindrical shape, a fibrous shape, and a planar substrate shape.

In a preferable embodiment, the photo-ligating nucleic acid may be immobilized onto a support by being directly bound thereto, but may also be immobilized onto a support via a linker moiety. The linker moiety may be a molecular species, preferably linear in shape, which is inert to the chemical reactions of nucleic acids, and has 5 or more, and preferably 10 or more, atoms. The linker moiety is preferably a nucleic acid such as DNA, RNA or PNA, polyethylene glycol, an alkane, or the like. Polyethylene glycol is particularly preferable, and hexa (ethylene glycol) can be suitably used. As the method for producing a nucleic acid immobilized onto a support, the immobilized nucleic acid can be produced by bonding the terminal phosphoric acid group of the nucleic acid to the linker moiety. The linker moiety and the nucleic acid may be bonded, and then the linker moiety may be bonded to the support, or on the contrary, the support and the linker moiety may be first bonded, and then the linker moiety may be bonded to the nucleic acid. In regard to the position at which the linker moiety is bonded to the nucleic acid, it is usually preferable to use the terminal phosphoric acid group, but the position is not intended to be limited to this. For example, the linker moiety may be bonded to a functional group of a base moiety present within the nucleic acid.

The process of hybridizing a photo-ligating nucleic acid and a target nucleic acid can be carried out under the conventional conditions (temperature, pH, salt concentration, buffer solution and the like) appropriate for hybridization, but it is preferable to carryout the process in the same reaction solution as that used in the subsequent process of performing light irradiation to induce photo-ligation, from the viewpoint of workability.

The hybridized photo-ligating nucleic acid and target nucleic acid can be photo-ligated by performing light irradiation. This photo-ligation corresponds to the crosslinking between molecules, since the photo-ligation occurs as an intermolecular covalent bonding is formed between the photo-ligating nucleic acid molecule and the target nucleic acid molecule as a result of a photoreaction of the artificial base moiety. A molecule and another molecule between which a crosslink has been formed as such, are not merely associated based on simple thermal stability only, and therefore, the molecules remain bonded without being dissociated, even in the case of being laid under the conditions in which a complementary double strand is dissociated.

According to a preferable embodiment, the process of photo-ligating is carried out in a reaction solution containing a salt which has a buffering action. Examples of the salt which has a buffering action include cacodylate, phosphate, and tris salt, but according to the present invention, it is preferable that the salt having a buffer action be cacodylate, from the viewpoint of enhancing the fluorescent intensity. It is preferable that the concentration of the salt having a buffering action be in the range of 5 to 250 mM, and particularly preferably in the range of 10 to 100 mM. According to a preferable embodiment, the pH of the reaction solution is preferably in the range of 6.5 to 8.0, more preferably 6.5 to 7.5, and particularly preferably 6.7 to 7.3. According to a preferable embodiment, it is preferable that the reaction solution contain the salts of an alkali metal and/or an alkaline earth metal. Examples of the salts of an alkali metal and/or an alkaline earth metal include sodium chloride and magnesium chloride, and a preferred example is sodium chloride.

For the light irradiation in the process of performing photo-ligation, it is preferable to use light having a wavelength in the range of generally 350 to 380 nm, preferably in the range of 360 to 370 nm, and more preferably 366 nm, and particularly preferred is a laser light having a short wavelength of 366 nm. According to a preferable embodiment, the photoreaction based on light irradiation is carried out for a reaction time within one second to several seconds, and preferably within one second. However, the light irradiation can also be carried out over more time, while the container is stirred, in consideration of the light transmission of the container and the solution.

After the process of photo-ligating, a process of removing any un-photo-ligated nucleic acid by washing is carried out. A molecule and another molecule between which a crosslink has been formed as such, are not merely associated based on simple thermal stability only, and therefore, the molecules remain bonded without being dissociated, even in the case of being laid under the conditions in which a complementary double strand is dissociated. Accordingly, the process of removing any un-photo-ligated nucleic acid by washing is carried out, preferably by washing under the washing conditions in which a complementary double strand is dissociated.

As the washing conditions in which a complementary double strand is dissociated, the generally known conditions for the dissociation of complementary double strands can be used. For example, a temperature in the range of 80 to 100° C., preferably 90 to 100° C., and particularly preferably 95 to 100° C. can be used. It is desirable if the temperature ranges from the value of the boiling point to a higher temperature to an achievable extent as long as the covalent bond is not broken down. The pH is not particularly limited as long as the covalent bond is not broken down, but since it is difficult to induce hydrolysis of the covalent bond, a pH close to neutrality is preferred. The type of the salt and the salt concentration are not particularly limited to an extent that a precipitation of the sample that is inadequate for the operation does not occur, and in general, the presence of a salt at an appropriate concentration (for example, about 0.1 M NaCl) is preferable so as to promote the dissociation of a complementary double strand. Furthermore, in order to promote the dissociation of a complementary double strand, for example, urea can be added as a denaturing agent. Furthermore, in order to promote the dissociation of a complementary double strand, for example, sodium dodecyl sulfate can be added as a surfactant. In addition, the conditions known to be contributing to the dissociation of a complementary double bond can be used.

It is an excellent feature of the present invention that the process of removing any un-photo-ligated nucleic acid by washing can be carried out by washing under severe washing conditions, but it is not always necessary to carry out the washing under severe conditions, and adequate washing conditions can be selected based on the degree of expected impurities (noise). For example, washing can be carried out using pure water, without using a salt, a surfactant, a denaturing agent or the like.

After the process of removing any un-photo-ligated nucleic acid by washing, the target nucleic acid can be recovered by carrying out a process of irradiating the hybridized photo-ligating nucleic acid and target nucleic acid with light to induce photo-cleavage. Thereby, the target nucleic acid having a particular base sequence included in a nucleic acid mixture can be finally purified and recovered. Since the photo-ligation and photo-cleavage induced by the photo-ligating nucleic acid of the present invention are reversible, the molecule of the target nucleic acid thus obtained is not at all damaged as compared with the original state as was present in the nucleic acid mixture. Furthermore, since the photo-ligation and photo-cleavage induced by the photo-ligating nucleic acid of the present invention are reversible, the molecule of the photo-ligating nucleic acid is also not damaged as compared with the original state, and accordingly, the photo-ligating nucleic acid according to the present invention can be repeatedly used.

For the light irradiation in the process of performing photo-cleavage, it is generally preferable to use light having a wavelength in the range of 310 to 345 nm, preferably in the range of 310 to 340 nm, more preferably in the range of 310 to 330 nm, even more preferably in the range of 310 to 320 nm, and still more preferably 312 nm, and particularly preferred is a laser light having a short wavelength of 312 nm. According to a preferable embodiment, the photoreaction based on light irradiation is carried out for a reaction time within one second to several seconds, and preferably within one second. However, the light irradiation can also be carried out over more time, while the container is stirred, in consideration of the light transmission of the container and the solution. The target nucleic acid released into the reaction solution by photo-cleavage can be recovered according to a known method.

The photo-ligating nucleic acid used in the present invention is a photo-ligating nucleic acid having a group represented by the following formula (I) as a base moiety:

[Chemical Formula 5]

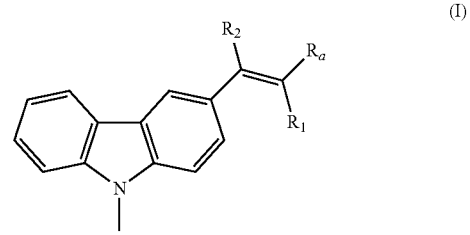

(I)

(wherein in the formula (I), Ra represents a cyano group, an amide group, a carboxyl group, a C2-C7 alkoxycarbonyl group or hydrogen; and R1 and R2 each independently represent a cyano group, an amide group, a carboxyl group, a C2-C7 alkoxycarbonyl group or hydrogen).

Such photo-ligating nucleic acids include a nucleic acid incorporated with a nucleoside (ribonucleoside) represented by the following formula (II):

[Chemical Formula 6]

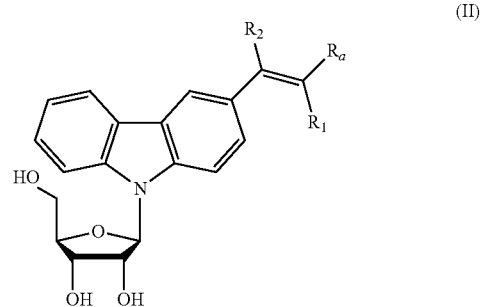

(II)

(wherein in the formula (II), Ra, R1 and R2 have the same definitions as stated for the formula (I)), and a nucleic acid incorporated with a nucleoside (deoxyribonucleoside) represented by the following formula (III):

[Chemical Formula 7]

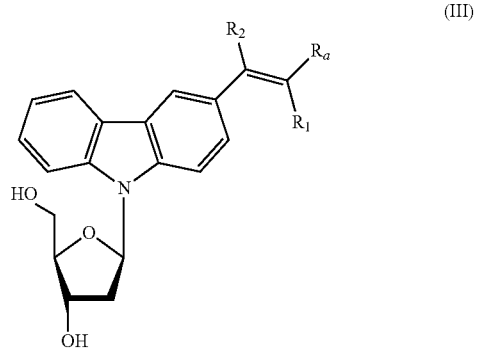

(III)

(wherein in the formula (III), Ra, R1 and R2 have the same definitions as stated for the formula (I)).

EXAMPLES

Hereinafter, the present invention will be described in detail by way of Examples. The present invention is not intended to be limited to the following Examples.

[1. Photo-Cleavage Reaction of Photo-Crosslinked Product Using 312 nm Light]

The structural formula of 3-cyanovinylcarbazole-1'-β-deoxyriboside ($^{CNV}$K), which is a photoresponsive nucleic acid, is presented in FIG. 1.

A photo-cleavage reaction was carried out with an aqueous solution (2 M aqueous urea:CH$_3$CN=1:1) of ODN(A$^{CNV}$K-GT) (20 μM), which is a photo-crosslinked product with thymine (total volume: 30 μL). The product was irradiated with light at 312 nm using a transilluminator at room temperature for 3 minutes (Scheme 1). The HPLC analysis results of the photoreaction product are presented in FIG. 2. Similarly, a photo-cleavage reaction was carried out with an aqueous solution (2 M aqueous urea:CH$_3$CN=1:1) of ODN(G$^{CNV}$K-GC) (20 μM), which is a photo-crosslinked product with cytosine (total volume: 30 μL). The product was irradiated with light at 312 nm using a transilluminator at room temperature for 3 minutes (Scheme 2). The HPLC analysis results of the photoreaction product are presented in FIG. 3. The changes over time are presented in FIG. 4. It was found that for any of the photo-cleavage reactions, the reaction proceeded efficiently on a basis of several minutes.

Scheme 1.

[Chemical Formula 8]

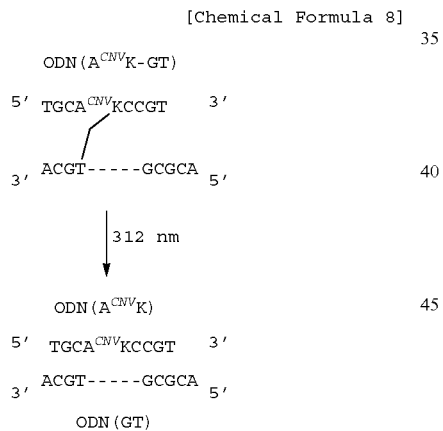

Scheme 2.

[Chemical Formula 9]

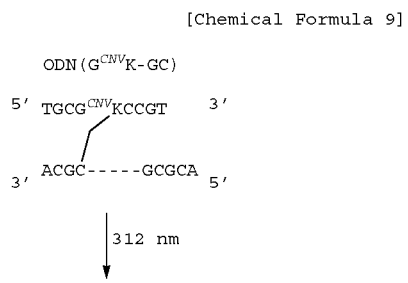

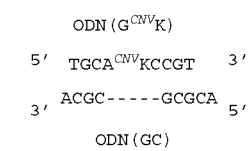

[2. Photo-Cleavage Reaction of Photo-Crosslinked Product Using 312-nm Light (Heating at 70° C.)]

A photo-cleavage reaction was carried out with an aqueous solution of ODN(A$^{CNV}$K-GT) (20 μM) (total volume: 30 μL). The product was irradiated with light at 312 nm using a transilluminator at 70° C. for 30 minutes (Scheme 3). The HPLC analysis results of the photoreaction product are presented in FIG. 5. The changes over time are presented in FIG. 6. A photo-cleavage reaction in an aqueous solution was carried out, and a crosslinked product having T at the crosslinking site underwent the reaction completely in 30 minutes.

Scheme 3.

[Chemical Formula 10]

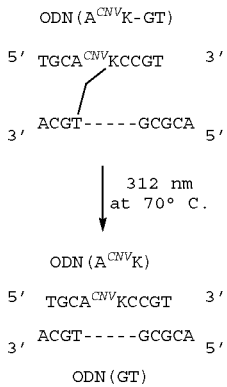

[3. Sequence-Specific Purification of DNA According to Photo-Genetic Engineering Method]

An outline of an example of the sequence-specific purification of DNA is presented in FIG. 7.

In order to purify DNA sequence-specifically, two kinds of DNA shown below were synthesized at a scale of 1 μmol. After the DNAs were synthesized, polystyrene beads (PS) were taken out, aqueous ammonia was added thereto, and the system was incubated at 55° C. for 15 hours to deprotect the DNAs. The PS was washed 5 times with MilliQ to adjust the pH to 7. Then, the products were dried over one hour with SpeedVac.

ODN1($^{CNV}$K)-PS: 5'-ATGA$^{CNV}$KGCGT-SSS-PS-3'

ODN2($^{CNV}$K)-PS: 5'-GTAA$^{CNV}$KTTCC-SSS-PS-3'

Sequence-specific purification of DNA using a solid phase was carried out according to Scheme 4.

Scheme 4.

[Chemical Formula 11]

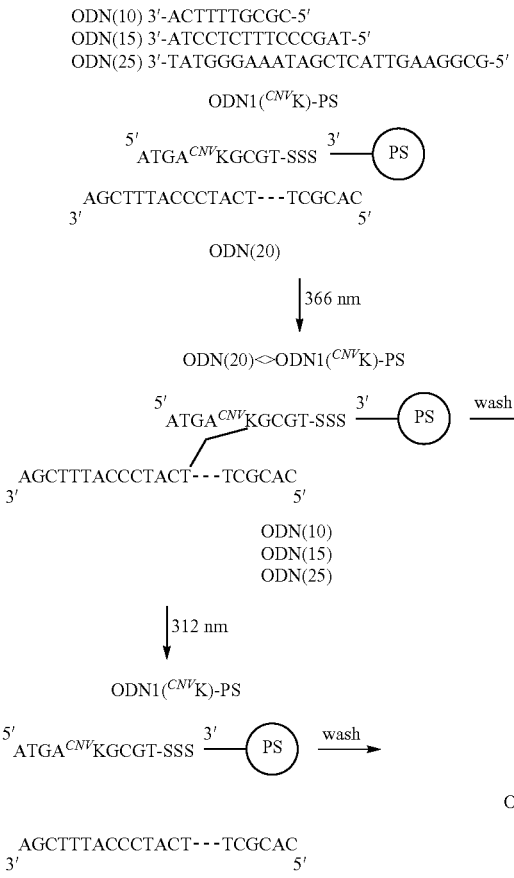

Scheme 5.

[Chemical Formula 12]

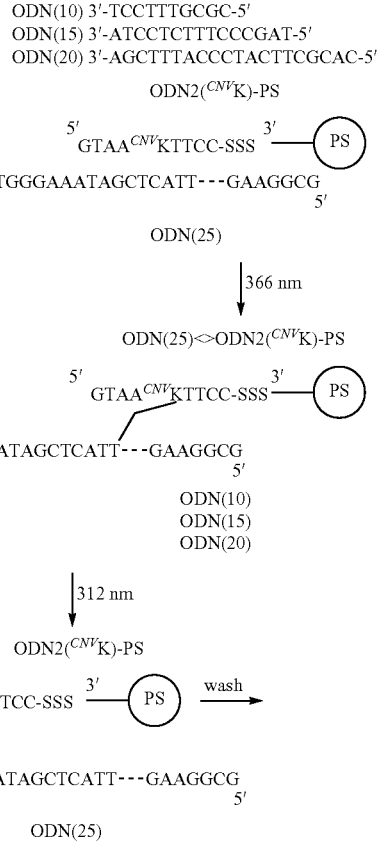

ODN(10), ODN(15), ODN(20) and ODN(25) were irradiated with light in the presence of ODN1($^{CNV}$K)-PS. In regard to the reaction conditions, ODN(10), ODN(15), ODN(20) and ODN(25) were respectively used at 25 μM, ODN1 ($^{CNV}$K)-PS (32 nmol/mg) was used in amount of 2 mg, a 50 mM cacodylic acid buffer (pH 7.0) and 1 M NaCl were used, and the total amount of solution was adjusted to 50 μL. The reaction solution prior to the light irradiation was analyzed by capillary gel electrophoresis (CGE) (FIG. 8(a)).

This reaction solution was irradiated with light at 366 nm for 15 minutes (the reaction solution was stirred in every 5 minutes) at 0° C. using a UV-LED. The supernatant solution of this reaction solution was analyzed by CGE (FIG. 8(b)). The supernatant solution was taken out and washed 5 times with ultrapure water. Ultrapure water (50 μL) was added to the solid phase support thus obtained, and the mixture was irradiated with light at 312 nm for 15 minutes and then analyzed by CGE (FIG. 8(c)).

When ODN1($^{CNV}$K)-PS was used, the desired ODN(20) could be recovered.

Sequence-specific purification of DNA using a solid phase was carried out according to Scheme 5.

ODN(10), ODN(15), ODN(20) and ODN(25) were irradiated with light in the presence of ODN2($^{CNV}$K)-PS. In regard to the reaction conditions, ODN(10), ODN(15), ODN(20) and ODN(25) were respectively used at 25 μM, ODN2 ($^{CVN}$K)-PS (32 nmol/mg) was used in amount of 2 mg, a 50 mM cacodylic acid buffer (pH 7.0) and 1 M NaCl were used, and the total amount of solution was adjusted to 50 μL. The reaction solution prior to the light irradiation was analyzed by capillary gel electrophoresis (CGE) (FIG. 9(a)).

This reaction solution was irradiated with light at 366 nm for 15 minutes (the reaction solution was stirred in every 5 minutes) at 0° C. using a UV-LED. The supernatant solution of this reaction solution was analyzed by CGE (FIG. 9(b)). The supernatant solution was taken out and washed 5 times with ultrapure water. Ultrapure water (50 μL) was added to the solid phase support thus obtained, and the mixture was irradiated with light at 312 nm for 15 minutes and then analyzed by CGE (FIG. 9(c)).

When ODN2($^{CNV}$K)-PS was used, the desired ODN(25) could be recovered.

[4. Photo-Crosslinking Reaction with RNA Using ODN Containing CNVK]

A photo-crosslinking reaction was carried out using an ODN containing $^{CNV}$K in a light irradiation time of one second. A photo-crosslinking reaction between ODN(A$^{CNV}$K) (20 μM) and RNA(GU) (20 μM) was carried out (sodium cacodylate 50 mM, NaCl 100 mM, total volume: 30 μL). The product was irradiated with light at 366 nm for one second at 0° C. using a UV-LED (Scheme 6). The HPLC analysis results of the photoreaction product are presented in FIG. 10. A photo-crosslinking reaction was carried out in a time of one second using RNA(GU), and the reaction proceeded efficiently with a yield of 86%. Thus, it was found that photomanipulation of RNA in a time of one second is possible.

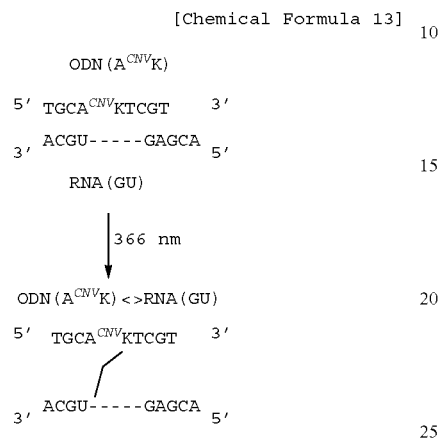

[5. Eight Kinds of Photo-Crosslinking Reactions Using ODN Containing CNVK]

Photo-crosslinking reactions were carried out using an ODN containing $^{CNV}$K. Photo-crosslinking reactions between ODN(A$^{CNV}$K) (10 μM) and RNA(XU) (X=A, G, C and U, 10 μM) were carried out (sodium cacodylate 50 mM, NaCl 100 mM, total volume: 200 μL). The products were irradiated with light at 366 nm for 20 seconds at 0° C. using a UV-LED, and the products were analyzed using UPLC. The results are presented in FIG. 11(*a*). Similarly, photo-crosslinking reactions were carried out using an ODN containing $^{CNV}$K in which C serves as the photo-crosslinking site. Photo-crosslinking reactions between ODN(G$^{CNV}$K) (10 μM) and RNA(XC) (X=A, G, C and U, 10 μM) were carried out (sodium cacodylate 50 mM, NaCl 100 mM, total volume: 200 μL). The products were irradiated with light at 366 nm for 20 seconds at 0° C. using a UV-LED, and the products were analyzed using UPLC. The results are presented in FIG. 11(*b*). From these results, it was found that the photo-crosslinking reactions with RNA proceed efficiently when the object of crosslinking is U or C.

[6. Photo-Cleavage Reaction of Photo-Crosslinked Products with RNA Using 312 nm Light]

A photo-crosslinked product ODN(A$^{CNV}$K)< >RNA(GU) or ODN(G$^{CNV}$K)< >RNA(GC), in which U or C is the photo-crosslinking site, was prepared by a photoreaction, and was collected by preparatory HPLC. Then, the mass of the photo-crosslinking product thus obtained was measured.

calcd. for ODN(A$^{CNV}$K)< >RNA(GU): [(M+H)$^+$] 5675.74, found 5675.25.

calcd. for ODN(G$^{CNV}$K)< >RNA(GC): [(M+H)$^+$] 5690.75, found 5690.68.

A photo-cleavage reaction was carried out with an aqueous solution of ODN(A$^{CNV}$K)< >RNA(GU) (2 M aqueous urea:CH$_3$CN=1:1) (total volume: 30 μL). The product was irradiated with light at 312 nm using a transilluminator at room temperature for one minute (Scheme 7). The HPLC analysis results of the photoreaction product are presented in FIG. 12. Similarly, a photo-cleavage reaction was carried out with ODN(G$^{CNV}$K)< >RNA(GC) (2 M aqueous urea:CH$_3$CN=1:1) (total volume: 30 μL). The product was irradiated with light at 312 nm using a transilluminator at room temperature for 3 minutes (Scheme 8). The HPLC analysis results of the photoreaction product are presented in FIG. 13. A photo-cleavage reaction was carried out using light at 312 nm, and a crosslinked product having U at the crosslinking site underwent the reaction completely in a time of one minute. Furthermore, a photo-cleavage reaction was carried out using light at 312 nm, and a crosslinked product having C at the crosslinking site underwent the reaction completely in a time of 3 minutes.

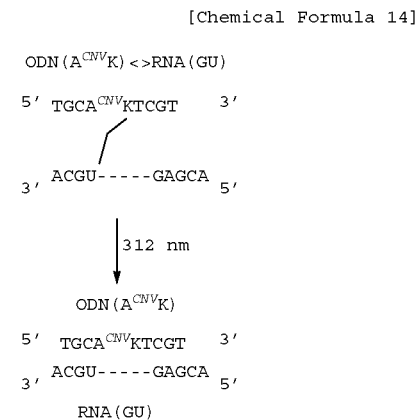

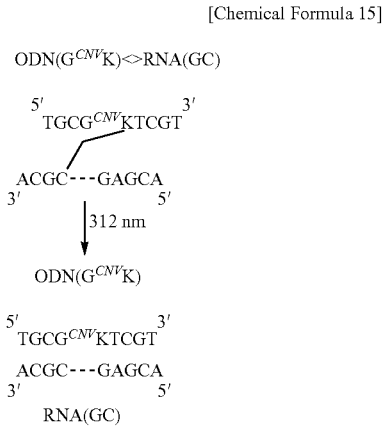

[7. Synthesis of ODN Carrying Vinylcarbazole as Base Moiety]

The synthesis was carried out according to the following Scheme 9. In the following explanation, a compound may be represented by the reference numeral assigned to the compound.

Scheme 9

[Chemical Formula 16]

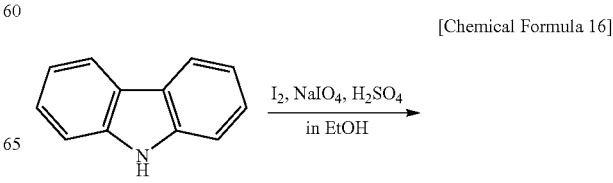

-continued

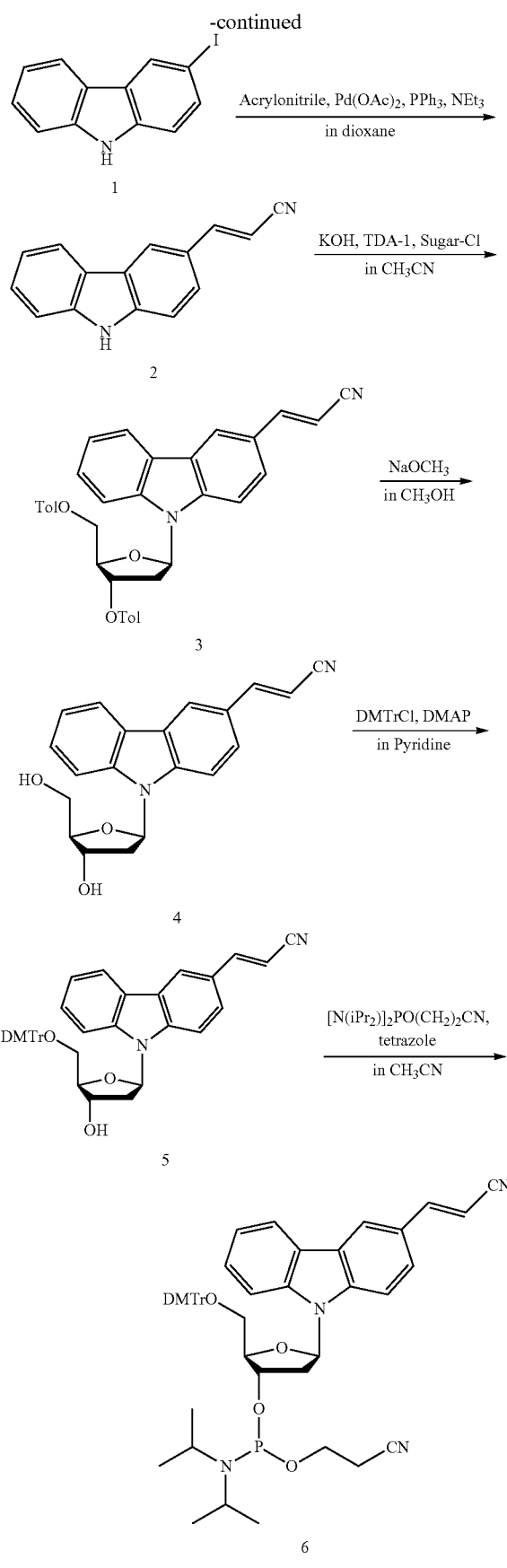

3-Iodocarbazole (1)

To an ethanol solution (500 mL) of carbazole (2.50 g, 15.0 mmol), NaIO$_4$ (0.80 g, 3.75 mmol) and I$_2$ (1.89 g, 7.45 mmol) were sequentially added, and then an ethanol solution (100 mL) of H$_2$SO$_4$ (1.60 mL, 30.0 mmol) was added. The reaction solution was refluxed for one hour at 65° C. The loss of raw materials was confirmed by TLC (HexH:AcOEt=4:1), and an ethanol solution (100 mL) of NaOH (1.4 g) was added thereto to neutralize the system. Ethanol was removed, and then the reaction solution was extracted two times with chloroform. The extract was washed two times with water. The organic phase was dried over Na$_2$SO$_4$, and the solvent was removed. The residue was purified by column chromatography (HexH: AcOEt=4:1), and thus compound 1 (3.06 g, 70%) was obtained as a white powder. Thus, 3,6-diiodocarbazole (0.47 g, 7.5%) was obtained as a white powder.

1: $^1$H NMR (DMSO-d$_6$) δ 11.4 (s, 1H), 8.49 (d, 1H, J=1.7 Hz), 8.14 (d, 1H, J=8.0 Hz), 7.62 (dd, 1H, J=8.4, 1.7 Hz), 7.48 (d, 1H, J=8.0 Hz), 7.40 (m, 1H), 7.33 (d, 2H, J=8.4 Hz), 7.16 (m, 1H).

3,6-Diiodocarbazole: $^1$H NMR (DMSO-d$_6$) δ 11.5 (s, 1H), 8.56 (d, 2H, J=1.7 Hz), 7.65 (dd, 2H, J=8.5, 1.7 Hz), 7.34 (d, 2H, J=8.5 Hz).

3-Cyanovinylcarbazole (2)

To a dioxane solution (10 mL) of triphenylphosphine (139 mg, 0.53 µmol), palladium acetate (40.0 mg, 0.18 µmol) and triethylamine (0.59 µL, 4.23 mmol) were sequentially added, and the mixture was stirred for 5 minutes at 75° C. A dioxane solution (15 mL) of compound 1 (1.03 g, 3.52 mmol) and acrylonitrile (0.46 µL, 7.04 mmol) were added, and the reaction solution was refluxed for 11.5 hours. The product was confirmed by TLC (HexH:AcOEt=4:1), and then the palladium powder was removed by cotton filtration. The product was purified by column chromatography (HexH:AcOEt=4: 1), and compound 2 (0.14 g, 18%, trans:cis=97:3) was obtained as a white powder, while compound 1 (0.37 g, recovery rate 37%) was recovered as a white powder.

2: $^1$H NMR (DMSO-d$_6$) δ 11.6 (s, 1H), 8.44 (s, 1H), 8.11 (d, 1H, J=8.0 Hz), 7.75 (d, 1H, J=16.7 Hz), 7.69-7.72 (m, 1H), 7.40-7.52 (m, 3H), 7.19-7.24 (m, 1H), 6.36 (d, 1H, J=16.7 Hz).

3-Cyanovinylcarbazole-1'-β-deoxyriboside-3',5'-di-(p-toluoyl)ester (3)

To an acetonitrile solution (20 mL) of KOH (0.22 g, 3.87 mmol) and TDA-1 (11 mg, 34 µmol), compound 2 (0.26 g, 1.20 mmol) was added at room temperature, and the mixture was stirred for 20 minutes. Chlorosugar (0.53 g, 1.24 mmol) was added to the reaction solution, and the mixture was stirred for 20 minutes at room temperature, and the loss of the raw materials was confirmed by TLC (HexH:AcOEt=4:1). The precipitates were removed, and then the reaction solution was purified by column chromatography (CHCl$_3$). Thus, compound 3 (0.23 g, 33%) was obtained as a yellow oil.

3: $^1$H NMR (CDCl$_3$) δ 8.09 (s, 1H), 8.02 (d, 2H, J=8.4 Hz), 7.98 (d, 2H, J=8.4 Hz), 7.62-7.65 (m, 1H), 7.62 (d, 1H, J=8.8 Hz), 7.49 (d, 1H, J=16.5 Hz), 7.25-7.31 (m, 7H), 7.17-7.20 (m, 1H), 6.68 (dd, 1H, J=9.3, 5.8 Hz), 5.78 (m, 1H), 5.76 (d, 1H, J=16.5 Hz), 4.91 (dd, 1H, J=12.4, 2.7 Hz), 4.78 (dd, 1H, J=12.4, 4.3 Hz), 4.55-4.57 (m, 1H), 3.09-3.20 (m, 1H), 2.45-2.52 (m, 1H), 2.45 (s, 3H), 2.44 (s, 3H), HRMS (MALDI): calcd. for C$_{36}$H$_{30}$N$_2$O$_5$Na [(M+Na)$^+$] 593.2053, found 593.2018.

3-Cyanovinylcarbazole-1'-β-deoxyriboside (4)

To a methanol solution (20 mL) of compound 3 (0.22 g, 0.39 mmol), 0.5 M methanolic NaOMe (2.3 mL, 1.2 mmol) and chloroform (5.0 mL) were added, and the reaction solution was stirred for 3.5 hours at room temperature. The loss of the raw materials was confirmed by TLC (CHCl$_3$:MeOH=9:1). The solvent was removed, and then the residue was purified by column chromatography (CHCl$_3$:MeOH=9:1). Thus, compound 4 (0.11 g, 81%) was obtained as a white powder.

4: $^1$H NMR (CDCl$_3$) δ 8.12 (d, 1H, J=1.7 Hz), 8.06 (d, 1H, J=7.7 Hz), 7.59 (d, 1H, J=9.1 Hz), 7.43-7.57 (m, 4H), 7.26-7.31 (m, 1H), 6.64 (dd, 1H, J=8.2, 6.9 Hz), 5.87 (d, 1H, J=16.5 Hz), 4.77-4.82 (m, 1H), 3.95-4.06 (m, 3H), 2.95 (dt, 1H, J=14.0, 8.2 Hz), 2.30 (ddd, 1H, J=14.0, 6.9, 3.3 Hz), HRMS (MALDI): calcd. for C$_{20}$H$_{18}$N$_2$O$_3$Na [(M+Na)$^+$] 357.1215, found 357.1265.

5'-O-(4,4'-dimethoxytrityl)-3-cyanovinylcarbazole-1'-β-deoxyriboside (5)

Pyridine (0.5 mL) was added to compound 4 (97 mg, 0.29 mmol) which had been azeotropically boiled with pyridine (1.0 mL×2). A pyridine solution (1.0 mL) of 4,4'-dimethoxytrityl chloride (118 mg, 0.35 mmol) and 4-(dimethylamino) pyridine (7.0 mg, 58 µmol) was added to the reaction solution, and the reaction solution was stirred for 18 hours at room temperature. The product was confirmed by TLC (CHCl$_3$: MeOH=95:5), and then pyridine was removed. The residue was purified by column chromatography (CHCl$_3$:MeOH=98:2), and thus compound 5 (113 mg, 61%) was obtained as a yellow powder.

5: $^1$H NMR (CDCl$_3$) δ 8.07 (d, 1H, J=1.7 Hz), 8.02-8.05 (m, 1H), 7.71 (d, 1H, J=8.5 Hz), 7.62-7.65 (m, 1H), 7.45-7.52 (m, 3H), 7.33-7.37 (m, 4H), 7.25-7.28 (m, 4H), 7.12 (dd, 1H, J=8.8, 1.7 Hz), 6.81 (dd, 4H, J=8.8, 1.7 Hz), 6.61 (dd, 1H, J=8.2, 6.3 Hz), 5.77 (d, 1H, J=16.7 Hz), 4.80-4.82 (m, 1H), 4.05-4.07 (m, 1H), 3.77 (s, 3H), 3.76 (s, 3H), 3.56-3.58 (m, 2H), 2.89 (dt, 1H, J=13.8, 8.2 Hz), 2.23 (ddd, 1H, J=13.8, 6.3, 2.7 Hz), 1.98 (d, 1H, J=3.6 Hz), HRMS (MALDI): calcd. for C$_{41}$H$_{36}$N$_2$O$_5$Na [(M+Na)$^-$] 659.2522, found 659.2485.

5'-O-(4,4'-dimethoxytrityl)-3-cyanovinylcarbazole-1'-β-deoxyriboside-3'-O-(cyanoethoxy-N,N-diisopropylamino)phosphoramidite (6)

Acetonitrile (1.5 mL) was added to compound 5 (0.11 g, 0.17 mol) which had been azeotropically boiled with acetonitrile (1.5 mL). An acetonitrile solution (0.37 mL, 0.17 mol) of 2-cyanoethyl-N,N,N',N'-tetraisopropylphosphorodiamidite (52 µL, 0.17 mol) and 0.45 M tetrazole was added to the reaction solution, and the reaction solution was stirred for 1.0 hour at room temperature. The reaction solution was extracted two times with deacetation-treated ethyl acetate, and the extract was washed with saturated aqueous NaHCO$_3$ and H$_2$O. The organic phase was dried over MgSO$_4$, and the solvent was removed. Compound 6 (0.12 g), which was a crude product as a yellow oil, was transferred into acetonitrile in a rubber-sealed bottle and was azeotropically boiled three times. Subsequently, the resultant was used in the DNA synthesis without further purification.

Synthesis of ODN Containing 3-cyanovinylcarbazole-1'-β-deoxyriboside ($^{CNV}$K)

The ODNs containing $^{CNV}$K as shown below were synthesized.

ODN(A$^{CNV}$K): 5'-TGCA$^{CNV}$KCCGT-3'

ODN(G$^{CNV}$K): 5'-TGCG$^{CNV}$KCCGT-3'

ODN(C$^{CNV}$K): 5'-TGCC$^{CNV}$KCCGT-3'

ODN(T$^{CNV}$K): 5'-TGCT$^{CNV}$KCCGT-3'

[Chemical Formula 17]

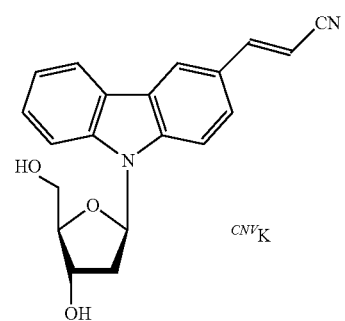

$^{CNV}$K

The syntheses were carried out according to the following Scheme 10.

Scheme 10

[Chemical Formula 18]

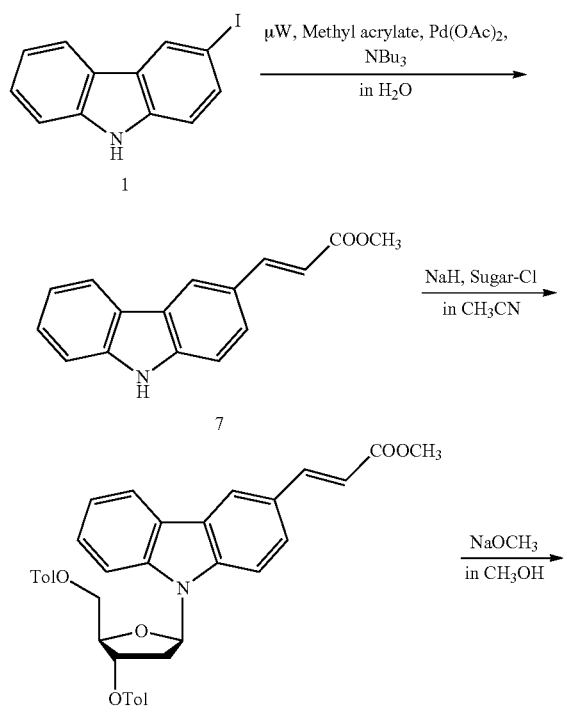

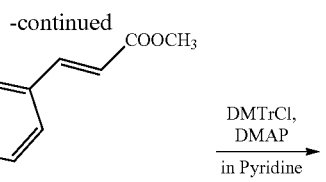

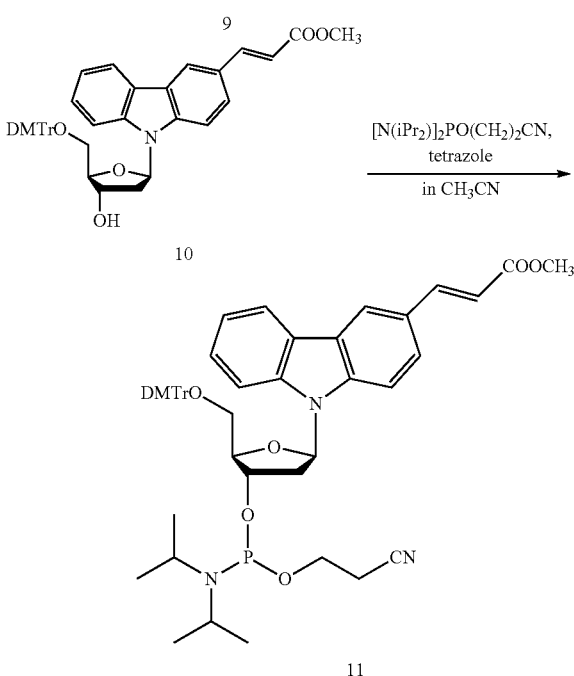

3-Methoxycarbonylvinylcarbazole (7)

To a DMF solution (0.25 mL) of palladium acetate (38.0 mg, 0.17 µmol), compound 1 (0.50 g, 1.71 mmol), tributylamine (0.41 µL, 1.71 mmol), methyl acrylate (0.38 L, 4.27 mmol), and H$_2$O (1.0 mL) were sequentially added. The reaction solution was allowed to react at 160° C. for 10 minutes using microwaves, and the reaction was traced by TLC. Thereby, the loss of compound 1 was confirmed. The palladium powder was removed by Kiriyama filtration, and then the reaction solution was purified by column chromatography (HexH:AcOEt=3:1), and thus compound 7 (0.26 g, 62%) was obtained as a white powder.

7: $^1$H NMR (CDCl$_3$) δ 8.26 (s, 1H), 8.21 (s, 1H), 8.07 (d, 1H, J=8.0 Hz), 7.89 (d, 1H, J=15.9 Hz), 7.61 (dd, 1H, J=1.7, 8.5 Hz), 7.39-7.44 (m, 3H), 7.23-7.29 (m, 1H), 6.47 (d, 1H, J=15.9 Hz), 3.81 (s, 3H).

3-Methoxycarbonylcarbazole-1'-β-deoxyriboside-3', 5'-di-(p-toluoyl)ester (8)

To an acetonitrile solution (49 mL) of compound 7 (0.55 g, 2.22 mmol), NaH (92.0 mg, 2.31 mmol) was added at room temperature, and the mixture was stirred for 10 minutes. Chlorosugar (1.14 g, 2.66 mmol) was added to the reaction solution, and the mixture was stirred for 60 minutes at room temperature. The loss of the raw materials was confirmed by TLC (HexH:AcOEt=4:1). After the precipitates were removed, the reaction solution was purified by column chromatography (HexH:AcOEt=4:1), and thus compound 8 (0.98 g, 71%) was obtained as a white powder.

3-Methoxycarbonylcarbazole-1'-β-deoxyriboside (9)

To a methanol solution (46 mL) of compound 8 (0.96 g, 1.59 mmol), 0.5 M methanolic NaOMe (9.6 mL, 4.8 mmol) and dichloromethane (12 mL) were added, and the reaction solution was stirred for one hour at room temperature. The loss of the raw materials was confirmed by TLC (CHCl$_3$:MeOH=9:1). After the solvent was removed, the residue was purified by column chromatography (CHCl$_3$:MeOH=9:1), and thus compound 9 (0.28 g, 48%) was obtained as a white powder.

9: $^1$H NMR (CDCl$_3$) δ 8.20 (s, 1H), 8.06 (d, 1H, J=7.7 Hz), 7.86 (d, 1H, J=15.9 Hz), 7.53-7.61 (m, 3H), 7.44 (t, 1H, J=7.1 Hz), 7.24-7.27 (m, 1H), 6.63 (dd, 1H, J=8.2, 7.0 Hz), 6.46 (d, 1H, J=15.9 Hz), 4.75-4.80 (m, 1H), 3.95-4.04 (m, 3H), 3.81 (s, 1H), 2.95 (dt, 1H, J=14.0, 8.2 Hz), 2.28 (ddd, 1H, J=14.0, 7.0, 3.6 Hz).

5'-O-(4,4'-dimethoxytrityl)-3-methoxycarbonylvinyl-carbazole-1'-β-deoxyriboside (10)

Pyridine (0.5 mL) was added to compound 9 (0.23 g, 0.63 mmol) which had been azeotropically boiled with pyridine (1.0 mL×2). A pyridine solution (2.2 mL) of 4,4'-dimethoxytrityl chloride (0.26 g, 0.75 mmol) and 4-(dimethylamino)pyridine (15.0 mg, 0.13 µmol) was added to the reaction solution, and the reaction solution was stirred for 16 hours at room temperature. The product was confirmed by TLC (CHCl$_3$:MeOH=95:5), and then pyridine was removed. The residue was purified by column chromatography (CHCl$_3$:MeOH=99:1), and thus compound 10 (0.21 g, 51%) was obtained as a yellow powder.

10: $^1$H NMR (CDCl$_3$) δ 8.17 (s, 1H), 8.02-8.05 (m, 1H), 7.83 (d, 1H, J=15.9 Hz), 7.62-7.66 (m, 3H), 7.46-7.49 (m, 2H), 7.34-7.38 (m, 4H), 7.25-7.28 (m, 4H), 7.15 (d, 1H, J=8.8 Hz), 6.81 (dd, 4H, J=8.8, 1.4 Hz), 6.61 (dd, 1H, J=8.5, 6.3 Hz), 6.40 (d, 1H, J=15.9 Hz), 4.76-4.80 (m, 1H), 4.05-4.09 (m, 1H), 3.80 (s, 3H), 3.77 (s, 3H), 3.76 (s, 3H), 3.56-3.57 (m, 2H), 2.89 (dt, 1H, J=14.0, 8.5 Hz), 2.18 (m, 1H), 2.17 (d, 1H, J=3.8 Hz).

5'-O-(4,4'-dimethoxytrityl)-3-methoxycarbonylvinyl-carbazole-1'-β-deoxyriboside-3'-O-(cyanoethoxy-N, N-diisopropylamino)phosphoramidite (11)

Acetonitrile (1.3 mL) was added to compound 10 (0.20 g, 0.29 µmol) which had been azeotropically boiled with acetonitrile (1.0 mL). An acetonitrile solution (0.65 mL, 0.29 µmol) of 2-cyanoethyl-N,N,N',N'-tetraisopropylphosphorodiamidite (92 µL, 0.29 µmol) and 0.45 M tetrazole was added to the reaction solution, and the reaction solution was stirred for 2 hours at room temperature. The reaction solution was extracted two times with deacetation-treated ethyl acetate, and the extract was washed with saturated aqueous NaHCO$_3$ and H$_2$O. The organic phase was dried over MgSO$_4$, and the solvent was removed. Compound 11 (0.25 g), which was a crude product as a yellow oil, was transferred into acetonitrile in a rubber-sealed bottle and was azeotropically boiled three times. Subsequently, the resultant was used in the DNA synthesis without further purification.

[Synthesis of Modified ODN]

ODN(AX) (5'-TGCAXCCGT-3', X=9) and ODN(GX) (5'-TGCGXCCGT-3', X=9) were synthesized using ABI 3400 DNA synthesizer. The CPG of each of the reaction mixtures thus obtained was divided into two, and one of the reaction mixtures was incubated at 37° C. for 17 hours using 0.4 M NaOH in H$_2$O:CH$_3$OH=1:4 to deprotect the product, neutralized with 2 M TEAA, and then freeze-dried. The other reaction mixture was incubated at room temperature for 17 hours using 0.05 M $K_2CO_3$ in $CH_3OH$ to deprotect the product, neutralized with 2 M TEAA, and then freeze-dried. The DNAs of ODN($A^{OHV}K$), ODN($G^{OHV}K$), ODN($A^{OMeV}K$) and ODN($G^{OMeV}K$) were purified by reverse phase HPLC. The DNAs were respectively subjected to enzymatic degradation. The isolation yield was 5, 10, 11 and 13%, respectively. The molecular weights were measured by MALDI-TOF-MS.

```
calcd. for ODN (A^OHVK), 5'-TGCA^OHVKCCGT-3':

[(M + H)^+] 2801.93, found 2802.12.

calcd. for ODN (G^OHVK), 5'-TGCG^OHVKCCGT-3':

[(M + H)^+] 2817.93, found 2818.08.

calcd. for ODN (A^OMeVK), 5'-TGCA^OMeVKCCGT-3':

[(M + H)^+] 2815.95, found 2816.07.

calcd. for ODN (G^OMeVK), 5'-TGCG^OMeVKCCGT-3':

[(M + H)^+] 2831.95, found 2831.98.
```

The ODNs containing $^{NH2V}K$ as shown below were synthesized.

```
ODN(A^NH2VK):  5'-TGCA^NH2VKCCGT-3'

ODN(G^NH2VK):  5'-TGCG^NH2VKCCGT-3'
```

[Chemical Formula 19]

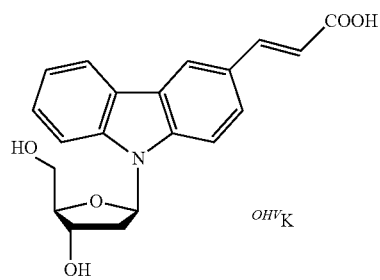

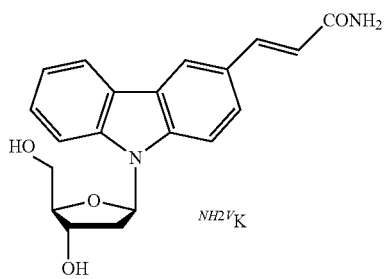

INDUSTRIAL APPLICABILITY

According to the present invention, purification and recovery of a nucleic acid having a particular base sequence can be carried out by achieving a good balance between high sequence-specificity and a high recovery rate. Purification and recovery of a nucleic acid having a single-base-substituted base sequence, which is attracting attention for the purpose of new drug development or genetic diagnosis, is also possible, and thus the present invention is industrially useful. Furthermore, the purification and recovery according to the present invention can be carried out in a very short time by subjecting an artificial base to photo-ligation and photo-cleavage. Accordingly, purification and recovery can also be achieved using an RNA which is susceptible to degradation and is short-lived, and thus the present invention is industrially useful.

The invention claimed is:

1. A method of purifying a target nucleic acid having a particular base sequence that is contained in a nucleic acid mixture, the method comprising:

hybridizing a photo-ligating nucleic acid (wherein the nucleic acid includes a nucleic acid and a peptide nucleic acid) having a group represented by the following formula (I) as a base moiety:

[Chemical Formula 20]

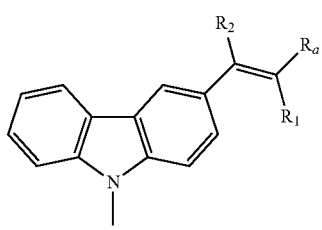

(I)

(wherein in the formula (I), Ra represents a cyano group, an amide group, a carboxyl group, a C2-C7 alkoxycarbonyl group or hydrogen; and $R_1$ and $R_2$ each independently represent a cyano group, an amide group, a carboxyl group, a C2-C7 alkoxycarbonyl group or hydrogen), with the target nucleic acid having a particular base sequence that is contained in a nucleic acid mixture;

irradiating the hybrid of the photo-ligating nucleic acid and target nucleic acid with light to induce photo-ligation of the hybrid;

removing any un-photo-ligated nucleic acid by washing; and irradiating the hybrid of the photo-ligating nucleic acid and the target nucleic acid with light to induce photo-cleavage of the hybrid.

2. The method according to claim 1, wherein the step of removing any un-photo-ligated nucleic acid by washing is carried out by washing under the washing conditions in which a complementary double strand is dissociated.

3. The method according to claim 1, wherein the photo-ligating nucleic acid has a labeling site.

4. The method according to claim 1, wherein the photo-ligating nucleic acid is immobilized onto a support.

5. The method according to claim 1, wherein the light irradiation of the step of inducing photo-ligation is carried out by irradiation with light having a wavelength in the range of 350 to 380 nm.

6. The method according to claim 1, wherein the light irradiation of the step of inducing photo-cleavage is carried out by irradiation with light having a wavelength in the range of 310 to 345 nm.

7. The method according to claim 1, wherein the step of inducing photo-ligation is carried out in a reaction solution containing a salt having a buffering action.

8. A photo-ligating nucleic acid (wherein the nucleic acid includes a nucleic acid and a peptide nucleic acid) having a labeling site and having a group represented by the following formula (I) as a base moiety:

[Chemical Formula 21]

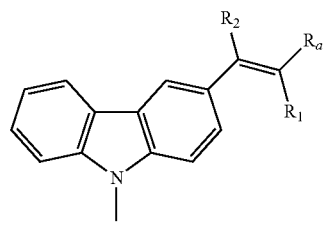

(I)

wherein in the formula (I), Ra represents a cyano group, an amide group, a carboxyl group, a C2-C7 alkoxycarbonyl group, or hydrogen; and $R_1$ and $R_2$ each independently represent a cyano group, an amide group, a carboxyl group, a C2-C7 alkoxycarbonyl group, or hydrogen.

9. A photo-ligating nucleic acid (wherein the nucleic acid includes a nucleic acid and a peptide nucleic acid) immobilized onto a support and having a group represented by the following formula (I) as a base moiety:

[Chemical Formula 22]

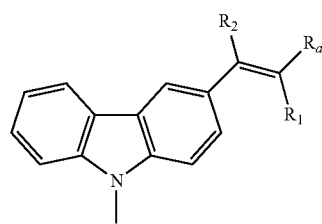

(I)

wherein in the formula (I), Ra represents a cyano group, an amide group, a carboxyl group, a C2-C7 alkoxycarbonyl group, or hydrogen; and $R_1$ and $R_2$ each independently represent a cyano group, an amide group, a carboxyl group, a C2-C7 alkoxycarbonyl group, or hydrogen.

* * * * *